United States Patent [19]

Henry et al.

[11] 4,329,355

[45] May 11, 1982

[54] MESOIONIC ANTITUMOR COMPOSITIONS AND METHODS FOR USING THE SAME IN THE TREATMENT OF CANCER

[76] Inventors: David W. Henry, 119 Meadowbrook Dr., Chapel Hill, N.C. 27514; Kenneth J. Ryan, 754 Lakemuir Dr., Sunnyvale, Calif. 94086; Edward W. Grange, 3480 Waverley St., Palo Alto, Calif. 94306

[21] Appl. No.: 16,384

[22] Filed: Mar. 1, 1979

[51] Int. Cl.$^3$ .............................................. A61K 31/42
[52] U.S. Cl. .................................................. 424/272
[58] Field of Search ........................................ 424/272

[56] References Cited

PUBLICATIONS

Masuda et al., Chem. Pharm. Bull., 19 (3), pp. 559–563 (1971).

Primary Examiner—Jerome D. Goldberg

[57] ABSTRACT

Mesoionic anhydro-5-amino-1,2,3,4-oxatriazolium hydroxides and methods of using the same in the treatment of cancer, said compositions containing, as an active ingredient, one or more compounds having the structure

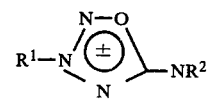

wherein $R^1$ represents a phenyl or substituted phenyl group and $R^2$ represents hydrogen or a methyl group.

8 Claims, No Drawings

MESOIONIC ANTITUMOR COMPOSITIONS AND METHODS FOR USING THE SAME IN THE TREATMENT OF CANCER

BACKGROUND OF THE INVENTION

The invention described herein was made in the course of or under a contract with the U.S. Department of Health, Education and Welfare.

The nearest known prior art is an article entitled "Studies on Mesoionic Compounds. III.[1]) Synthesis of ψ-3-Aryl-5-imino-3,5-dihydro-1-oxa-2,3,4-triazole Hydrochlorides and Their Derivatives" by Katsutada Masuda, Takaaki Kamiya, and Kenichi Kashiwa, published in the *Chemical & Pharmaceutical Bulletin* 19 (3) pp. 559 through 563 (1971). Among others, this article discloses compounds corresponding to the above structured formula, alleged to have utility as hypotensive agents, wherein $R^1$ represents phenyl, o-tolyl and p-chlorophenyl and $R^2$ is hydrogen. No compounds are disclosed wherein $R^2$ is methyl or other lower alkyl group.

SUMMARY OF INVENTION

The present invention rests, in part, on the discovery that mesoionic anhydro-5-imino-1,2,3,4-oxatriazolium hydroxides, usually in the form of their pharmaceutically acceptable salts, have utility as anticancer agents when administered to cancerous warm-blooded animals. Said compounds are those having the structure

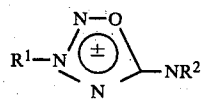

wherein $R^1$ represents phenyl or substituted phenyl group and $R^2$ represents hydrogen or a methyl group. Illustrative substituted phenyl groups represented by $R^1$ include those wherein the phenyl nucleus is substituted, at one position or another about the ring, with methyl, chloro or nitro groups. In one embodiment, this aspect of the invention relates to a process for treating leukemia which comprises administering to a warm-blooded animal having an abnormal proportion of leukocytes a therapeutic amount of a mesoionic compound of the type described above. These compounds (usually in the form of their HCl or other pharmaceutically acceptable salts) can be administered either per se or in association with a pharmaceutically acceptable diluent or carrier. Accordingly, the invention also provides a pharmaceutical composition in dosage unit form comprising from about 0.1 to 500 mg of the active compound, per dosage unit, together with a pharmaceutically acceptable nontoxic, inert carrier or diluent therefor. Lastly, the present invention discloses particular novel compounds coming within the scope of the broad class of mesoionic compounds.

The novel compounds of the present invention to which claim is made are identified hereinafter by the numbers 1, 2 and 3, they forming the subject of Examples I, II and III, respectively. Among these new compounds, 1 is particularly preferred, it having the structure presented above wherein $R^1$ represents phenyl and $R^2$ represents methyl. The novel compounds are:

Anhydro-5-methylamino-3-phenyl-1,2,3,4-oxatriazolium hydroxide hydrochloride (Cpd 1)
Anhydro-5-amino-3-(m-tolyl)-1,2,3,4-oxatriazolium hydroxide hydrochloride (Cpd 2)
Anhydro-5-amino-3-(m-nitrophenyl)-1,2,3,4-oxatriazolium hydroxide hydrochloride (Cpd 3)

The compounds are prepared as follows:

EXAMPLE I

To 15 g (71 mols) of 4-methyl-1-phenyl-3-thiosemicarbazide in 300 ml absolute ethanol was added with chilling 21 ml of conc. HCl. To this mixture was added slowly, keeping temperature below 10° C., 6 g of sodium nitrite in 10 ml of water. The mixture was stirred on an ice bath for ½ hr to give a yield of 7.6 g (50%) of 1, light yellow-white solid, mp. 184°–188° dec (from ethyl acetate).

A small sample from an earlier run was converted to the free base, a yellow-brown solid mp 67°–68° and analyzed. See Table 1 for analytical results.

EXAMPLE II 23.8 g (0.15 mol) of m-tolylhydrazine hydrochloride was freed from the hydrochloride, dissolved in 900 ml of ethyl acetate and treated with 8.75 g (0.0825 mol) of cyanogen bromide at −10° with stirring. After 45 min at this temperature, the reaction mixture was filtered to remove the precipitate of the hydrazine hydrobromide and then cooled to −30°. A solution of about 18 g (0.2 mol) of nitrogen dioxide in 225 ml of ether was added over 1 hr and stirred another hr at that temperature. Then addition of 120 ml of 3% HCl gave 6.7 g (42% yield) of 2 as a white solid. See Table 1 for other properties.

This procedure for Cpd 2, using nitrogen dioxide ($NO_2 \rightleftharpoons N_2O_4$), is a modification of Masuda et al. (Table 1, footnote 2) which uses dry gaseous nitrous acid ($N_2O_3$). In our hands, $NO_2$ gave more reproducible results.

The known compounds, 4, 5, and 6 were all obtained by the procedure used for Cpd 2 as white solids. See Table 1.

EXAMPLE III

Starting with 0.15 mol of m-nitrophenylhydrazine hydrochloride, the same procedure used for Cpd 2 afforded 3 in 10% yield as a light yellow solid. See Table 1.

TABLE 1

| | | | PROPERTIES OF THE MESOIONIC COMPOUNDS | | | | | |
|---|---|---|---|---|---|---|---|---|
| | | | Analysis | | | | | |
| | | | Calc'd. % | | | Found, % | | |
| Compound | mp, °C. | Formula | C | H | N | C | H | N |
| 1 | 184–188[a] | $C_8H_8N_4O$ | 54.5 | 4.58 | 31.8 | 54.4 | 4.67 | 31.7 |
| 2 | 162 | $C_8H_8N_4O \cdot HCl \cdot 0.9 H_2O$ | 42.0 | 4.75 | 24.5 | 42.0 | 4.41 | 28.8 |
| 3 | 191 | $C_7H_5N_5O_3 \cdot HCl$ | 34.5 | 2.48 | 28.8 | 34.2 | 2.46 | 28.7 |
| 4 | 192[b] | known[b] | | | | | | |
| 5 | 195[b] | known[b] | | | | | | |

TABLE 1-continued
PROPERTIES OF THE MESOIONIC COMPOUNDS

| Compound | mp, °C. | Formula | Calc'd. % C | H | N | Found, % C | H | N |
|---|---|---|---|---|---|---|---|---|
| 6 | 162[b] | known[b] | | | | | | |

[a] mp and solubility as the HCl salt; analysis was on the free base.
[b] Literature m.p. are 195–197°, 196° and 166–8° for 4,5 and 6, respectively. See (a) K. Masuda and T. Kamitani, Japanese Patent 70 20,904, July 15, 1 70 (Chem. Abstr., 73, 87930 g (1970)) and K. Masuda, T. Kamiya and K. Kashiwa, Chem. Pharm. Bull. 19, 559 (1971).
All six of the compounds shown on this table are soluble in water and in hot ethyl acetate.

As described above, Cpd. 1 was prepared in both the salt as well as the free form. Cpds. 2 and 3, as well as known compounds 4, 5 and 6 (where $R^2$ is —H and $R^1$ is phenyl, p-chlorophenyl and o-tolyl, respectively) were prepared in the form of water-soluble, acid addition salts. While HCl was employed in these examples as the salt forming acid, other pharmaceutically acceptable, non-toxic addition salts with acids such as nitric, sulfuric, phosphoric or glycolic could be used.

The compounds used in a practice of this invention, including any salts thereof, can be administered to the animal by any available route, including oral and parenteral (intravenous, intraperitoneal, subcutaneous, and intramuscular) administration. The amount administered is sufficient to ameliorate the leukemia or other type of cancer against which the compounds hereof may prove to be effective, and will depend upon the type of cancer, the species of animal, and the weight of the animal. A dosage of a compound of the present invention within the range from about 0.1 mg/kg to about 500 mg/kg per day should be sufficient to ameliorate leukemia. In the treatment of lower test animals, a similar dosage range is therapeutic. The upper limit dosage is that imposed by toxic side effects.

To facilitate administration, the compounds employed in a practice of this invention, including the salts thereof, can be provided in composition form, and preferably in dosage unit form. While any compound selected can be administered per se, it is normally administered in conjunction with a pharmaceutically acceptable carrier therefor, which dilutes the compound and facilitates handling. The term "pharmaceutically acceptable" means that the carrier (as well as the resulting composition) is sterile and nontoxic.

The carrier or diluent can be solid, semisolid, or liquid, and can serve as a vehicle, excipient, or medium for the anti-cancer agent. Exemplary diluents and carriers include lactose, dextrose, sucrose, sorbitol, mannitol, starches, gum acacia, calcium phosphate, mineral oil, cocoa butter, oil of theobroma, aliginates, tragacanth, gelatin, syrup, methyl cellulose, polyoxyethylene sorbitan, mono-laurate, methyl- and propyl-hydroxybenzoate, talc or magnesium stearate, as well as sterile water.

For convenience in handling, the compounds employed in a practice of this invention and the carrier or diluent can be enclosed or encapsulated in a capsule, sachet, cachet, gelatin, paper or other container, especially when intended for use in dosage units. The dosage units can for example take the form of tablets, capsules, suppositories or cachets, and of solutions or dispersions in an aqueous medium.

The following examples illustrate various forms of dosage units in which the compound of Example I can be prepared, said compound being typical of the other compounds which can be employed in a practice of this invention.

EXAMPLE IV

| Tablet formulation | Mg/tablet |
|---|---|
| Compound 1 | 15 |
| Lactose | 86 |
| Cornstarch (dried) | 45.5 |
| Gelatin | 2.5 |
| Magnesium stearate | 1.0 |

Compound 1 is powdered and passed through a mesh sieve and well mixed with the lactose and 30 mg of the cornstarch, both passed through a sieve. The mixed powders are massed with a warm gelatin solution, prepared by stirring the gelatin in water and heating to form a 10% w/w solution. The mass is granulated by passing through a sieve and the moist granules dried at 40° C.

The dried granules are regranulated by passing through a sieve and the balance of the starch and the magnesium stearate is added and thoroughly mixed.

The granules are compressed to produce tablets each weighing 150 mg.

EXAMPLE V

| Tablet formulation | Mg/tablet |
|---|---|
| Compound 1 | 100 |
| Lactose | 39 |
| Cornstarch (dried) | 80 |
| Gelatin | 4.0 |
| Magnesium stearate | 2.0 |

The method of preparation is identical with that of Example IV except that 60 mg of starch is used in the granulation process and 20 mg during tableting.

EXAMPLE VI

| Capsule formulation | Mg/tablet |
|---|---|
| Compound 1 | 250 |
| Lactose | 150 |

Compound 1 and lactose are passed through a sieve and the powders well mixed together before filling into hard gelatin capsules of suitable size, so that each capsule contains 400 mg of mixed powders.

EXAMPLE VII

| Suppositories | Mg/suppository |
|---|---|
| Compound 1 | 50 |
| Oil of Theobroma | 950 |

Compound 1 is powdered and passed through a sieve and triturated with molten oil of theobroma at 45° C. to form a smooth suspension. The mixture is well stirred and poured into molds, each of nominal 1 g capacity, to produce suppositories.

EXAMPLE 8

| Cachets | Mg/cachet |
|---|---|
| Compound 2 | 100 |
| Lactose | 400 |

Compound 1 is passed through a mesh sieve, mixed with lactose previously sieved and fitted into cachets of suitable size so that each contains 500 mg.

EXAMPLE IX

| Intermuscular injection (sterile suspension in aqueous vehicle) | Mg |
|---|---|
| Compound 1 | 10 |
| Sodium citrate | 5.7 |
| Sodium carboxymethyl-cellulose (low viscosity grade) | 2.0 |
| Methyl para-hydroxybenzoate | 1.5 |
| Propyl para-hydroxybenzoate | 0.2 |
| Water for injection to 1.0 ml | |

EXAMPLE X

| Intraperitoneal, intravenous or subcutaneous injection (sterile solution in aqueous carrier system) | Mg |
|---|---|
| Compound 1 hydrochloric acid addition salt | 15 |
| Sodium citrate | 5.7 |
| Sodium carboxymethyl-cellulose (low viscosity grade) | 2.0 |
| Methyl para-hydroxybenzoate | 1.5 |
| Propyl para-hydroxybenzoate | 0.2 |
| Water for injection to 1.0 ml | |

The other compounds useful in a practice of this invention can be prepared in dosage unit form in the same general fashion as that described above for Cpd 1.

BIOLOGICAL TESTS

Biological testing data for the compounds of this invention are presented in Table 2 given below. Said data were obtained when these compounds were tested against lymphocytic leukemia P388 implanted in mice under the auspices of the National Cancer Institute (NCI) and according to protocols which use the increased survival time of treated animals compared to controls as the measure of antitumor efficiency. In carrying out these tests, the various doses were administered ip in the form of aqueous dispersions or emulsions, the latter being formed in many cases with the aid of hydroxypropylcellulose.

TABLE 2

HETEROCYCLES OF STRUCTURE 

ACTIVITY AGAINST LYMPHOCYTIC LEUKEMIA P388 IN THE MOUSE[d]
(All as HCl salts)

| Compound | NSC No. | $R^1$ | $R^2$ | \multicolumn{9}{c}{P388 qd 1-9; % T/C at doses (mg/kg)} |
|---|---|---|---|---|---|---|---|---|---|---|---|---|
| | | | | 400 | 200 | 100 | 50 | 25 | 12.5 | 6.25 | 3.13 | 1.56 |
| 1 | 176330 | $C_6H_5$ | Me | | | 3/6[a] | tox | 170[e] | 136 | 134 | 111 | |
| 2 | 276746 | $C_6H_4Me$—m | H | | | 1/6 | tox | 135 | 116 | 110 | 106 | |
| | | | | | | tox | 167 | 152 | 114 | 100 | 100 | |
| 3 | 278171 | $C_6H_4NO_2$—m | H | | | 0/6 | 4/6 | 121 | 137 | 110 | 106 | |
| | | | | | | | 113 | 139 | 127 | 113 | 113 | |
| 4 | 265204 | $C_6H_5$ | H | | | 0/6 | tox[b] | 195 | 150 | 142 | 117 | 110 |
| | | | | | | 2/6 | tox | 189 | 137 | 117 | 108 | |
| 5 | 266208 | $C_6H_4Cl$—p | H | | | 2/6 | 151 | 137 | 133 | 102 | 108 | |
| | | | | | | 0/6 | 88 | 155 | 124 | 124 | | |
| 6 | 267214 | $C_6H_4Me$—o | H | | | 0/6 | 146 | 129 | 120 | 113 | 101 | |
| | | | | | | 4/6[c] | tox | 141 | 130 | 106 | | |

[a]Toxicity as indicated by Day 5 survivors over total animals at start.
[b]Toxicity as indicated by % T/C < 85.
[c]Doses (mg/kg) in this experiment were: 75, 50, 33, 22, and 14.7.
[d]Ip P388 murine leukemia treated ip on QD1-9 schedule according to Standard NCI protocols. Assay described in R. I. Geran, N. H. Greenberg, M. M. MacDonald, A. M. Schumacher and B. J. Abbott, Cancer Chemother. Rep., Part 3, 3 (No. 2), 9 (1972), Protocol 1,200. T/C = ratio of survival time of treated mice to that of untreated controls times 100. Untreated controls survive about 9 days.
[e]Mean and Standard deviation for 16 experiments was 154 ± 24.

What is claimed is:

1. A process for treating leukemia which comprises administering to a warm-blooded animal having an abnormal proportion of leukocytes an effective amount for treating leukemia of a compound selected from the group having the structure

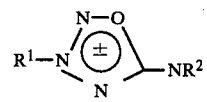

wherein $R^1$ represents phenyl or phenyl substituted by methyl, nitro or chloro groups, and wherein $R^2$ represents hydrogen or a methyl group, together with their pharmaceutically acceptable salts.

2. A process according to claim 1 in which the compound is administered in an effective amount for treating leukemia within a range of from about 0.1 to about 500 mg per day.

3. The process of claim 2 wherein the compound administered to the warm-blooded animal is anhydro-5-methylamino-3-phenyl-1,2,3,4-oxatriazolium hydroxide hydrochloride.

4. The process of claim 2 wherein the compound administered to the warm-blooded animal is anhydro-5-amino-3-(m-tolyl)-1,2,3,4,-oxatriazolium hydroxide hydrochloride.

5. The process of claim 2 wherein the compound administered to the warm-blooded animal is anhydro-5-amino-3-(m-nitrophenyl)-1,2,3,4-oxatriazolium hydroxide hydrochloride.

6. The process of claim 2 wherein the compound administered to the warm-blooded animal is anhydro-5-amino-3-phenyl-1,2,3,4-oxatriazolium hydroxide hydrochloride.

7. The process of claim 2 wherein the compound administered to the warm-blooded animal is anhydro-5-amino-3-(p-chlorophenyl)-1,2,3,4,-oxatriazolium hydroxide hydrochloride.

8. The process of claim 2 wherein the compound administered to the warm-blooded animal is anhydro-5-amino-3-(o-tolyl)-1,2,3,4,-oxatriazolium hydroxide hydrochloride.

* * * * *